United States Patent [19]

Krämer et al.

[11] 4,153,692
[45] May 8, 1979

[54] ACYLATED IMIDAZOLYL-O,N-ACETALS, THEIR PHARMACEUTICALLY ACCEPTABLE SALTS AND METAL COMPLEXES

[75] Inventors: Wolfgang Krämer; Karl H. Büchel; Manfred Plempel, all of Wuppertal, Fed. Rep. of Germany

[73] Assignee: Bayer Aktiengesellschaft, Fed. Rep. of Germany

[21] Appl. No.: 872,901

[22] Filed: Jan. 27, 1978

Related U.S. Application Data

[62] Division of Ser. No. 764,830, Feb. 2, 1977.

[30] Foreign Application Priority Data

Feb. 7, 1976 [DE] Fed. Rep. of Germany ....... 2604865

[51] Int. Cl.² .................. A61K 31/415; A61K 31/555
[52] U.S. Cl. ..................................... 424/245; 260/299; 424/273 R; 548/341
[58] Field of Search ................. 424/273, 245; 548/341

[56] References Cited

U.S. PATENT DOCUMENTS 3,892,764 7/1975 Metzger et al. ...................... 548/341

FOREIGN PATENT DOCUMENTS 2333355 4/1975 Fed. Rep. of Germany.

Primary Examiner—Allen J. Robinson
Attorney, Agent, or Firm—Jacobs & Jacobs

[57] ABSTRACT

Acylated imidazolyl-O,N-acetals of the formula

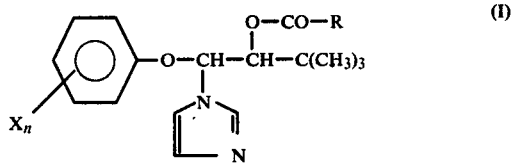

and their pharmaceutically acceptable salts and metal complexes wherein
  R is alkyl, alkenyl, alkinyl, cycloalkyl, halogenoalkyl, optionally substituted phenyl, optionally substituted phenoxyalkyl, alkylamino, dialkylamino or optionally substituted phenylamino;
  X is halogen, alkyl, cycloalkyl, alkoxy, halogenoalkyl, alkylthio, alkoxycarbonyl, optionally substituted phenyl, optionally substituted phenoxy, optionally substituted phenylalkyl, amino, cyano or nitro; and
  n is 0 or an integer of from 1 to 5;
are useful as antimicrobial agents, particularly for their use in treating mycotic infections in humans and animals.

36 Claims, No Drawings

ACYLATED IMIDAZOLYL-O,N-ACETALS, THEIR PHARMACEUTICALLY ACCEPTABLE SALTS AND METAL COMPLEXES

CROSS-REFERENCE

This is a division of Ser. No. 746,830 filed Feb. 2, 1977.

The present invention relates to the use of new acylated imidazolyl-O,N-acetals, pharmaceutically-acceptable, nontoxic salts thereof and metal complexes thereof as antimicrobial agents, particularly as anti-mycotic agents. It is known that imidazolyl-O,N-acetals, and especially 1-imidazolyl-1-phenoxy-3,3-dimethylbutan-2-ols, exhibit good antimycotic activity (see German OLS No. 2,333,355). However, the action of those compounds is not entirely satisfactory, particularly against dermatophytes.

We have now discovered that acylated imidazolyl-O,N-acetals of the formula

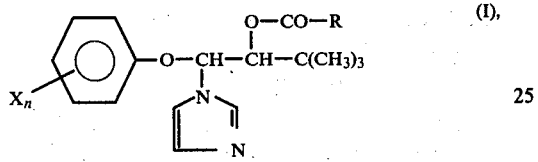

pharmaceutically acceptable salts thereof and metal complexes thereof, wherein

R is alkyl, especially of 1 to 18 carbon atoms, and particularly 1 to 12 carbon atoms; alkenyl, especially of 2 to 4 carbon atoms; alkinyl, especially of 2 to 4 carbon atoms; cycloalkyl, especially of 5 to 7 carbon atoms; halogenoalkyl, especially of 1 to 4 carbon atoms in the alkyl moiety and 1 to 5 halogen atoms; phenyl unsubstituted or substituted by halogen, cyano, nitro or alkyl, especially of 1 to 4 carbon atoms; phenoxyalkyl, especially of 1 or 2 carbon atoms in the alkyl moiety, unsubstituted or nuclear-substituted by halogen, amino, cyano, nitro or alkyl of 1 to 4 carbon atoms; alkylamino, especially lower alkylamino; dialkylamino, especially di-lower alkylamino; or phenylamino unsubstituted or nuclear-substituted by halogen, nitro or cyano;

X is halogen; alkyl, especially lower alkyl; cycloalkyl, especially of 5 to 7 carbon atoms; alkoxy, especially of 1 to 4 carbon atoms; halogenoalkyl, especially of 1 to 4 carbon atoms in the alkyl moiety and 1 to 5 halogen atoms; alkylthio, especially of 1 to 4 carbon atoms in the alkyl moiety; alkoxy-carbonyl, especially of 1 to 4 carbon atoms in the alkoxy moiety; phenyl unsubstituted or substituted by halogen, amino, cyano, nitro or alkyl, especially of 1 or 2 carbon atoms; phenoxy unsubstituted or nuclear-substituted by halogen, amino, cyano, nitro or alkyl, especially of 1 or 2 carbon atoms; amino; cyano; or nitro; and n is 0 or an integer from 1 to 5;

exhibit good antimicrobial properties and are particularly useful as antimycotics. In the above-referred-to formula, when n is an integer from 2 to 5 and therefore there is more than one X present in the phenyl moiety, the X's may be the same or different.

According to one embodiment of the present invention

R is alkyl of 1 to 8 carbon atoms; alkenyl of 2 to 4 carbon atoms; alkinyl of 2 to 4 carbon atoms; halogenoalkyl of 1 or 2 carbon atoms in the alkyl moiety and 1 to 5 halogen atoms selected from the group consisting of fluorine or chlorine; cycloalkyl of 5 to 7 carbon atoms; phenyl unsubstituted or substituted by halogen, cyano, nitro or alkyl of 1 or 2 carbon atoms; phenoxyalkyl of 1 or 2 carbon atoms in the alkyl moiety unsubstituted or nuclear-substituted by halogen, amino, cyano, nitro or alkyl of 1 or 2 carbon atoms; alkylamino of 1 to 4 carbon atoms in the alkyl moiety; dialkylamino of 1 to 4 carbon atoms in each alkyl moiety; or phenylamino unsubstituted or nuclear-substituted by halogen, nitro or cyano;

X is halogen; amino; cyano; nitro; alkyl of 1 to 4 carbon atoms; cycloalkyl of 5 to 7 carbon atoms; halogenoalkyl of 1 or 2 carbon atoms in the alkyl moiety and 1 to 5 halogen atoms selected from the group consisting of fluorine and chlorine; alkoxycarbonyl of 1 to 4 carbon atoms in the alkoxy moiety; alkoxy of 1 to 2 carbon atoms; alkylthio of 1 or 2 carbon atoms; phenyl unsubstituted or substituted by halogen, amino, cyano, nitro or alkyl of 1 or 2 carbon atoms; phenoxy unsubstituted or substituted by halogen, amino, cyano, nitro or alkyl of 1 or 2 carbon atoms; or phenylalkyl of 1 or 2 carbon atoms in the alkyl moiety unsubstituted or substituted in the alkyl portion by alkylcarbonyl of up to 3 carbon atoms in total and unsubstituted or substituted in the phenyl portion by halogen, nitro or cyano; and n is 0 or an integer from 1 to 3.

According to another embodiment of the present invention

R is alkyl of 1 to 6 carbon atoms; alkenyl of 2 to 4 carbon atoms; alkinyl of 2 to 4 carbon atoms; halogenoalkyl of 1 or 2 carbon atoms in the alkyl moiety and 1 to 5 halogen atoms selected from the group consisting of fluorine or chlorine; cyclohexyl; phenyl unsubstituted or substituted by halogen, cyano, nitro or alkyl of 1 or 2 carbon atoms; phenoxyalkyl of 1 or 2 carbon atoms in the alkyl moiety unsubstituted or nuclear-substituted by halogen, amino, cyano, nitro or alkyl of 1 or 2 carbon atoms; alkylamino of 1 or 2 carbon atoms in the alkyl moiety; dialkylamino of 1 to 4 carbon atoms in each alkyl moiety; or phenylamino unsubstituted or nuclear-substituted by halogen, nitro or cyano; X is halogen; amino; cyano; nitro; alkyl of 1 to 4 carbon atoms; cyclohexyl; halogenoalkyl of 1 to 2 carbon atoms in the alkyl moiety and 1 to 5 halogen atoms selected from the group consisting of fluorine and chlorine; alkoxycarbonyl of 1 to 4 carbon atoms in the alkoxy moiety; alkoxy of 1 or 2 carbon atoms; alkylthio of 1 or 2 carbon atoms; phenyl unsubstituted or substituted by halogen, amino, cyano, nitro or alkyl of 1 or 2 carbon atoms; phenoxy unsubstituted or nuclear-substituted by halogen, amino, cyano, nitro or alkyl of 1 or 2 carbon atoms; or phenylalkyl of 1 or 2 carbon atoms in the alkyl moiety unsubstituted or substituted in the alkyl portion by alkylcarbonyl of up to 3 carbon atoms in total and unsubstituted in the phenyl portion or substituted in the phenyl portion by halogen, nitro or cyano; and n is 0 or an integer from 1 to 3.

According to another embodiment of the present invention

R is alkyl of 1 to 4 carbon atoms; alkenyl of 2 to 4 carbon atoms; alkinyl of 2 to 4 carbon atoms; cycloalkyl of 5 or 6 carbon atoms; phenyl unsubstituted or substituted by chlorine; phenoxyalkyl of 1 or 2 carbon atoms in the alkyl moiety; alkylamino of 1 or 2 carbon atoms; dialkylamino of 1 or 2 carbon atoms; or phenylamino unsubstituted or nuclear-substituted by chlorine;

X is halogen; alkyl of 1 to 4 carbon atoms; cycloalkyl of 5 or 6 carbon atoms; trifluoromethyl; alkylthio of 1 or 2 carbon atoms; alkoxycarbonyl of 1 or 2 carbon atoms in the alkoxy moiety; phenyl unsubstituted or substituted by halogen; phenoxy unsubstituted or substituted by halogen; phenylalkyl of 1 or 2 carbon atoms in the alkyl moiety; or nitro; and n is 0 or an integer from 1 to 3.

According to another embodiment of the present invention

R is alkyl of 1 to 4 carbon atoms, allyl, cyclohexyl, phenyl unsubstituted or substituted by chlorine, phenoxymethyl, alkylamino of 1 or 2 carbon atoms, dimethylamino or chlorophenylamino;

X is chlorine, alkyl of 1 to 4 carbon atoms, cyclopentyl, cyclohexyl, trifluoromethyl, methylthio, alkoxycarbonyl of 1 or 2 carbon atoms in the alkoxy moiety, phenyl unsubstituted or substituted by halogen, phenoxy unsubstituted or substituted by halogen, benzyl or nitro; and n is 0 or an integer from 1 to 3.

According to another embodiment of the present invention

R is alkyl of 1 to 18 carbon atoms, halogenoalkyl of 1 to 4 carbon atoms in the alkyl moiety and 1 to 3 halogen atoms, alkylamino of 1 to 4 carbon atoms in the alkyl portion or phenylamino unsubstituted or nuclear-substituted by chlorine;

X is halogen, cycloalkyl of 5 or 6 carbon atoms, phenyl or chlorophenyl; and n is 0 or an integer from 1 to 3.

According to another embodiment of the present invention

R is methyl, butyl, heptadecyl, methylamino, tert.-butylamino, phenylamino or chlorophenylamino;

X is fluorine, chlorine, bromine, iodine, cyclohexyl, phenyl or chlorophenyl; and n is 0 or an integer from 1 to 3.

The compounds of formula (I) have two asymmetric carbon atoms and can, therefore, be in the erythro or the threo form. Preferably, they are racemic.

The compounds of the present invention may be prepared by reacting an imidazole derivative of the formula (II)

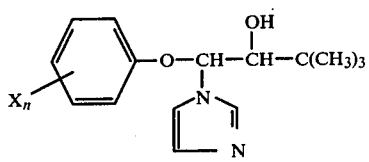

wherein X and n are as above defined, according to the four Process Variants A to D set forth below. The imidazole derivatives of the formula (II) are known from German OLS No. 2,333,355.

PROCESS VARIANT A

Imidazole derivatives of the formula (II) may be reacted with acid halides according to procedures per se known; for example, in molar amounts in the presence of an inert organic solvent, such as ethyl acetate at temperatures of between 0° C. and 100° C. The compounds of formula (I) are obtained in the form of their hydro-halides and can be isolated as such by precipitating them utilizing an organic solvent, such as hexane, filtering them off and optionally purifying them by recrystallization. The compounds of formula (I) can also be isolated in the form of their free bases by adding aqueous sodium bicarbonate solution to the reaction mixture and isolating the base according to procedures per se known.

PROCESS VARIANT B

Imidazole derivatives of the formula (II) may be reacted with acid anhydrides according to procedures per se known; such as, for example, in molar amounts in the presence of an inert organic solvent, such as acetone or an excess of the acid anhydride, and in the presence of an acidic or basic catalyst, such as sodium acetate, at a temperature of from 0° C. to 105° C., followed by isolation of the compounds of formula (I) according to procedures per se known.

PROCESS VARIANT C

Imidazole derivatives of the formula (II) may be reacted with ketenes according to procedures per se known; for example, in molar amounts in the presence of an inert organic solvent, such as ethyl acetate, and in the presence of an acidic or basic catalyst, such as sodium acetate, at temperatures of from −10° C. to +70° C., followed by isolation of the compounds of formula (I) according to procedures per se known.

PROCESS VARIANT D

Imidazole derivatives of the formula (II) may be reacted with isocyanates according to procedures per se known; for example, in molar amounts in the presence of an inert organic solvent, such as ethyl acetate, and in the presence of a catalyst, such as triethylamine, at temperatures of from 0° C. to 100° C., followed by isolation of the compounds of formula (I) according to procedures per se known.

The compounds of formula (I) form salts with pharmaceutically acceptable acids. These acids include the hydrogen halide acids such as hydrochloric acid and hydrobromic acid, especially hydrochloric acid, and phosphoric acid, nitric acid and monofunctional and bifunctional carboxylic acids and hydroxycarboxylic acids such as, for example, acetic acid, maleic acid, succinic acid, formaric acid, tartaric acid, citric acid, salicyclic acid, sorbic acid, lactic acid and 1,5-naphthalene disulphonic acid.

The salts of compounds of the formula (I) can be obtained in a simple manner by procedures per se known for forming salts, such as by dissolving the base in an ether, such as diethyl ether, and adding the appropriate acid, isolating the salt according to procedures per se known, such as by filtering off, and, optionally, purifying the salt.

Compounds of the formula (I) may also be present in the form of complexes with metal salts. Metals which may be mentioned for these complexes are preferably metals of main groups II to IV and of sub-groups I, II and IV to VIII of the periodic table, especially copper, zinc, manganese, magnesium, tin, iron and nickel. Suitable salts include the pharmaceutically acceptable salts which are formed with acids such as those set forth above. Preferred acids include the hydrogen halide acids such as hydrochloric acid and hydrobromic acid, and phosphoric acid, nitric acid and sulphuric acid.

The metal complexes of the present invention can be obtained in a simple manner by procedures per se known; for example, by dissolving the metal salt in an alcohol, for example, ethanol, and adding the solution to the base. Isolation is accomplished in a manner per se known; for example, by filtering off, and, optionally, purifying by recrystallization.

Representative compounds according to the present invention include the following:

2-acetoxy-1-phenoxy-1-imidazol-1-yl-3,3-dimethyl-butane,
2-acetoxy-1-(4-chlorophenoxy)-1-imidazol-1-yl-3,3-dimethyl-butane,
2-acetoxy-1-(2-chlorophenoxy)-1-imidazol-1-yl-3,3-dimethyl-butane,
2-acetoxy-1-(2,4,5-trichlorophenoxy)-1-imidazol-1-yl-3,3-dimethyl-butane,
2-acetoxy-1-(4-nitro phenoxy)-1-imidazol-1-yl-3,3-dimethyl-butane,
2-acetoxy-1-(2-cyclopentylphenoxy)-1-imidazol-1-yl-3,3-dimethyl-butane,
2-acetoxy-1-(3-trifluoromethylphenoxy)-1-imidazol-1-yl-3,3-dimethyl-butane,
2-acetoxy-1-(4-methylphenoxy)-1-imidazol-1-yl-3,3-dimethyl-butane,
2-acetoxy-1-(4-methoxycarbonylphenoxy)-1-imidazol-1-yl-3,3-dimethyl-butane,
2-acetoxy-1-(3-ethoxyphenoxy)-1-imidazol-1-yl-3,3-dimethyl-butane,
2-acetoxy-1-(4-methylthiophenoxy)-1-imidazol-1-yl-3,3-dimethyl-butane,
2-acetoxy-1-(4,4'-chlorophenylphenoxy)-1-imidazol-1-yl-3,3-dimethyl-butane,
2-acetoxy-1-(4-chloro-2-methylphenoxy)-1-imidazol-1-yl-3,3-dimethyl-butane,
2-acetoxy-1-(4-phenoxyphenoxy)-1-imidazol-1-yl-3,3-dimethyl-butane,
2-acetoxy-1-(3,4-dimethylphenoxy)-1-imidazol-1-yl-3,3-dimethyl-butane,
2-acetoxy-1-(4,4'-iodobiphenoxy)-1-imidazol-1-yl-3,3-dimethyl-butane,
2-acetoxy-1-(4-benzylphenoxy)-1-imidazol-1-yl-3,3-dimethyl-butane,
2-ethylcarbonyloxy-1-phenoxy-1-imidazol-1-yl-3,3-dimethyl-butane.
2-ethylcarbonyloxy-1-(4-chlorophenoxy)-1-imidazol-1-yl-3,3-dimethyl-butane,
2-ethylcarbonyloxy-1-(2-phenylphenoxy)-1-imidazol-1-yl-3,3-dimethyl-butane,
2-isopropylcarbonyloxy-1-phenoxy-1-imidazol-1-yl-3,3-dimethyl-butane,
2-isopropylcarbonyloxy-1-(4-fluorophenoxy)-1-imidazol-1-yl-3,3-dimethyl-butane,
2-tert.-butylcarbonyloxy-1-phenoxy-1-imidazol-1-yl-3,3-dimethyl-butane,
2-butylcarbonyloxy-1-(4-bromophenoxy)-1-imidazol-1-yl-3,3-dimethyl-butane,
2-propenylcarbonyloxy-1-(2,5-dichlorophenoxy)-1-imidazol-1-yl-3,3-dimethyl-butane,
2-allylcarbonyloxy-1-(4-tert.-butylphenoxy)-1-imidazol-1-yl-3,3-dimethyl-butane,
2-propynylcarbonyloxy-1-(4-cyclohexylphenoxy)-1-imidazol-1-yl-3,3-dimethyl-butane,
2-cyclohexylcarbonyloxy-1-phenoxy-1-imidazol-1-yl-3,3-dimethyl-butane,
2-phenylcarbonyloxy-1-(5-chloro-2-methylphenoxy)-1-imidazol-1-yl-3,3-dimethyl-butane,
2-(4-chlorophenylcarbonyloxy)-1-(2-chlorophenoxy)-1-imidazol-1-yl-3,3-dimethyl-butane,
2-phenoxymethylcarbonyloxy-1-(4-phenylphenoxy)-1-imidazol-1-yl-3,3-dimethyl-butane,
2-phenoxymethylcarbonyloxy-1-(4-chlorophenoxy)-1-imidazol-1-yl-3,3-dimethyl-butane,
2-ethylcarbamoyloxy-1-(2,4-dichlorophenoxy-1-imidazol-1-yl-3,3-dimethyl-butane,
2-dimethylcarbamoyloxy-1-(4-nitrophenoxy)-1-imidazol-1-yl-3,3-dimethyl-butane,
2-methylcarbamoyloxy-1-(2,4,5-trichlorophenoxy)-1-imidazol-1-yl-3,3-dimethyl-butane,
2-methylcarbamoyloxy-1-(2-phenylphenoxy)-1-imidazol-1-yl-3,3-dimethyl-butane,
2-methylcarbamoyloxy-1-(3,4-dimethylphenoxy)-1-imidazol-1-yl-3,3-dimethyl-butane,
2-methylcarbamoyloxy-1-(2-methyl-5-chlorophenoxy)-1-imidazol-1-yl-3,3-dimethyl-butane,
2-methylcarbamoyloxy-1-(4-chloro-3,5-dimethyl-phenoxy)-1-imidazol-1-yl-3,3-dimethyl-butane,
2-phenylcarbamoyloxy-1-phenoxy-1-imidazol-1-yl-3,3-dimethyl-butane, and
2-(4-chlorophenylcarbamoyloxy)-1-(4-phenylphenoxy)-1-imidazol-1-yl-3,3-dimethyl-butane.

The compounds of formula (I), their pharmaceutically acceptable salts and metal complexes display a broad antimycotic spectrum of activity, especially against dermatophytes and blastomyces and also bi-phase fungi, for example, against *Candida* species such as *Candida albicans, Epidermophyton* species such as *Epidermophyton floccosum, Aspergillus* species such as *Aspergillus niger, Trichophyton* species such as *Trichophyton mentagrophytes, Microsporon* such as *Microsporon felineum,* and *Penicillium* species such as *Penicillium commune.*

The compounds of the present invention, their pharmaceutically acceptable salts and metal complexes are thus particularly useful for treating dermatomycoses, systemic mycoses caused by *Trichophyton mentagrophytes* and other Trichophyton species, *Microsporon* species, *Epidermophyton floccosum,* blastomyces and biphase fungi, as well as molds, in humans and in treating dermatomycoses, systemic mycoses and especially those caused by the above-mentioned pathogens in animals.

The pharmaceutical compositions of the present invention contain a major or minor amount, e.g., 0.1% to 99.5%, preferably 0.5% to 90% of at least one active compound as above defined in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 10 mg/kg to 300 mg/kg of body weight per day and preferably from 50 mg/kg to 200 mg/kg of body weight per day. In some instances a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as, for example, starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above and, optionally, with a binder such as carboxymethyl cellulose, an alginate, gelatin or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. An an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers, such as ethoxylated isostearyl alcohols and polyoxyethylene sorbitol esters, preservatives, flavor additives such as peppermint oil or saccharin, and the like, can also be added.

Where appropriate, dosage unit formulations for oral administration can be microencapsulated. The formulation can also be prepared to prolong or sustain the release as, for example, by coating or embedding particulate material in polymers, wax, or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as, for example, myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carriers as talc, bentonite, silicic acid, polyamide powder and the like. Liquid and semi-liquid formulations can utilize such carriers, in addition to those described above, as polyethylene glycol, vegetable and mineral oils, alcohols such as isopropanol, and the like. Other excipients such as emulsifiers, preservatives, colorants, perfumes and the like can also be present. Formulations can also be administered as an aerosol, utilizing the usual propellants such as the chlorofluorohydrocarbons.

While the routes of administration include oral, parenteral (i.e., intramuscular, intraperitoneal and intravenous), rectal and topical, parenteral administration, especially intravenous, is particularly preferred.

Examples A and B, set forth below, illustrate the antimycotic activity of the compounds of the present invention.

EXAMPLE A

Antimycotic in vitro activity

Description of the experiment

The in vitro tests were carried out in a series dilution test using germ inocula with an average of $5 \times 10^4$ germs/ml of substrate. The nutrient medium used was a) for dermatophytes and molds: Sabouraud's milieu d'epreuve and b) for yeasts: meat extract/glucose broth.

The incubation temperature was 28° C. and the incubation time was 24 to 96 hours.

Table A

Antimycotic in vitro activity

| Active compound | MIC values in γ/ml of nutrient medium with | | | | |
|---|---|---|---|---|---|
| | Trichophyton mentagrophytes | Microsporum felinum | Penicillium commune | Aspergillus niger | Candida albicans |
| 3-Cl-C₆H₄-O-CH(N-imidazolyl)-CH(OH)-C(CH₃)₃ (known) | 64 | — | >64 | — | 32 |
| 4-(CH₃)₃C-C₆H₄-O-CH(N-imidazolyl)-CH(OH)-C(CH₃)₃ (known) | 32 | — | >64 | — | 64 |
| C₆H₅-O-CH(N-imidazolyl)-CH(OH)-C(CH₃)₃ (known) | 32 | >64 | >64 | >64 | 32 |
| 4-Cl-C₆H₄-O-CH(N-imidazolyl)-CH(O-CO-CH₃)-C(CH₃)₃ (2) | 4 | 32 | 32 | 64 | 32 |
| 4-biphenylyl-O-CH(N-imidazolyl)-CH(O-CO-CH₃)-C(CH₃)₃ (4) | <1 | 8 | 8 | <1 | 64 |
| 4-Br-C₆H₄-O-CH(N-imidazolyl)-CH(O-CO-CH₃)-C(CH₃)₃ (5) | 4 | 32 | 32 | 64 | 64 |
| 4-I-C₆H₄-O-CH(N-imidazolyl)-CH(O-CO-CH₃)-C(CH₃)₃ (13) | 4 | 32 | 64 | 64 | 32 |
| 4'-Cl-biphenylyl-O-CH(N-imidazolyl)-CH(O-CO-CH₃)-C(CH₃)₃ (9) | <1 | 32 | 64 | 64 | 32 |

Table A-continued

Antimycotic in vitro activity

| Active compound | MIC values in γ/ml of nutrient medium with | | | | |
|---|---|---|---|---|---|
| | Trichophyton mentagrophytes | Microsporum felinum | Penicillium commune | Aspergillus niger | Candida albicans |
| H—⌬—⌬—O—CH—CH—C(CH₃)₃ with O—CO—CH₃ and N-imidazolyl (6) | 8 | — | 32 | — | 64 |

EXAMPLE B

Antimycotic in vivo activity on candidosis in mice

Description of the experiment

Mice of the SPF-CF$_1$ type were infected intravenously with 1–2 × 10$^6$ logarithmically-growing Candida cells, which were suspended in physiological sodium chloride solution. One hour before and seven hours after the infection the animals were treated orally with, in each case, 100 mg of the formulations per kg of body weight.

Untreated animals died of the infection 3 to 6 days after infection. The survival rate on the 6th day after infection was about 5% in the case of the untreated control animals

Table B

Antimycotic in vivo activity on candidosis in mice

| Active compound | Action |
|---|---|
| 3-Cl-C₆H₄—O—CH(OH)—CH(N-imidazolyl)—C(CH₃)₃ (known) | + |
| 4-(CH₃)₃C-C₆H₄—O—CH(OH)—CH(N-imidazolyl)—C(CH₃)₃ (known) | NA |
| 4-Cl-C₆H₄—O—CH(OCOCH₃)—CH(N-imidazolyl)—C(CH₃)₃ (2) | ++++ |
| 4-Br-C₆H₄—O—CH(OCOCH₃)—CH(N-imidazolyl)—C(CH₃)₃ (5) | ++ |
| C₆H₅—O—CH(OCOCH₃)—CH(N-imidazolyl)—C(CH₃)₃ (1) | ++ |
| 4-Cl-biphenyl—O—CH(OCOCH₃)—CH(N-imidazolyl)—C(CH₃)₃ (9) | ++++ |
| 4-F-C₆H₄—O—CH(OCOCH₃)—CH(N-imidazolyl)—C(CH₃)₃ (3) | +++ |
| 4-I-C₆H₄—O—CH(OCOCH₃)—CH(N-imidazolyl)—C(CH₃)₃ (13) | + |

++++ = good action = ≧ 80% survivors on the 6th day after infection
+++ = action = ≧ 60% survivors on the 6th day after infection
++ = weak action = ≧ 40% survivors on the 6th day after infection
+ trace action = < 40% survivors on 6th day after infection
NA = no action The following non-limitative examples more particularly illustrate the present invention:

EXAMPLE 1

C₆H₅—O—CH(OCOCH₃)—CH(N-imidazolyl)—C(CH₃)₃

(Process variant A)

8.0 g (0.1 mol) of acetyl chloride are added to 20.6 g (0.1 mol) of 1-imidazol-1-yl-1-phenoxy-3,3-dimethylbutan-2-ol in 100 ml of ethyl acetate at room temperature. The mixture is then heated under reflux for 4 hours. It is allowed to cool and concentrated by distilling off the solvent in vacuo. The residue is taken up in benzene and the solution is washed with aqueous sodium bicarbonate solution and dried over sodium sulphate. The solvent is distilled off under a water pump vacuum and the residue is recrystallized from petroleum ether. 20.6 g (45% of theory) of 2-acetoxy-1-phenoxy-1-imidazol-1-yl-3,3-dimethyl-butane are obtained as a mixture of isomers with a melting point of 114°–121° C.

Starting material

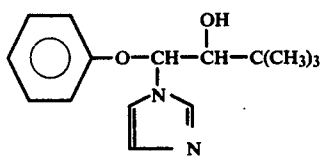

25.8 g (0.1 mol) of 1-imidazol-1-yl-1-phenoxy-3,3-dimethyl-butan-2-one are dissolved in 250 ml of methanol and 5.9 g (0.15 mol) of sodium borohydride are introduced in portions into this solution, at 5° C. to 10° C., while stirring and with reflux cooling. After stirring for 15 hours at room temperature, 20 ml of concentrated hydrochloric acid are added and the reaction mixture is stirred for a further 15 hours at room temperature and poured into 300 ml of saturated sodium bicarbonate solution. The mixture is extracted with twice 100 ml of methylene chloride, the organic phase is washed with twice 100 ml of water and dried over sodium sulphate and the solvent is distilled off under a water pump vacuum. The residue is ground with 30 ml of petroleum ether. 21.6 g (83% of theory) of 1-imidazol-1-yl-1-phenoxy-3,3-dimethyl-butan-2-ol are obtained as a mixture of isomers with a melting point of 99°–105° C.

EXAMPLE 2

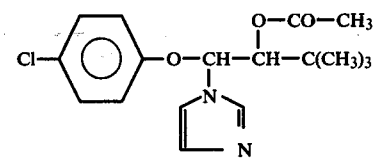

(Process variant B)

8.0 g (0.027 mol) of 1-(4-chlorophenoxy)-1-imidazol-1-yl-3,3-dimethyl-butan-2-ol are heated in 40 ml of acetic anhydride with 0.15 g of sodium acetate for 10 hours at 100° C. The solution is then cooled and stirred into 400 ml of ice water, the temperature being kept at 20°–25° C. The mixture is left to stand overnight. A smeary crystalline mass precipitates out and is taken up in chloroform. The chloroform solution is washed several times with water and sodium bicarbonate solution, dried over sodium sulphate and concentrated in vacuo by distilling off the solvent. The crystalline residue is boiled up in petroleum ether and the product is filtered off cold and dried. 4.5 g (49% of theory) of 2-acetoxy-1-(4-chlorophenoxy)-1-imidazol-1-yl-3,3-dimethylbutane are obtained as a mixture of isomers with a melting point of 81°–91° C.

EXAMPLES 3–23

The compounds below set forth in tabular form are produced in a manner analogous to that described in Examples 1 and 2.

General formula:

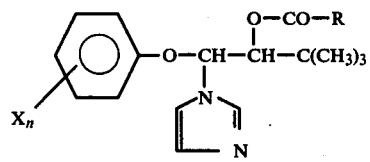

| Example No. | $X_n$ | R | Melting point (° C.) as a mixture of isomers |
|---|---|---|---|
| 3 | 4-F | CH₃ | 144–53 |
| 4 | 4-phenyl | CH₃ | 117–24 |
| 5 | 4-Br | CH₃ | 78–89 |
| 6 | 4-⟨H⟩phenyl | CH₃ | 254–57 (X½ naphthalene-1,5-disulfonate) |
| 7 | 2-phenyl | CH₃ | 161–74 (X½ naphthalene-1,5-disulfonate) |

-continued

| Example No. | $X_n$ | R | Melting point (° C.) as a mixture of isomers |
|---|---|---|---|
| 8 | 2-(cyclohexyl/phenyl) | CH₃ | 250–56, decomposition (X½ naphthalene-1,5-disulfonic acid) |
| 9 | 4-(C₆H₄)-Cl | CH₃ | 118–29 |
| 10 | 2-Cl,4-(phenyl) | CH₃ | 92–97 |
| 11 | 3-Br | CH₃ | 260–62 (X½ naphthalene-1,5-disulfonic acid) |
| 12 | 2,6-Cl₂,4-(phenyl) | CH₃ | 246–51 (X½ naphthalene-1,5-disulfonic acid) |
| 13 | 4 - J | CH₃ | 100–06 |
| 14 | 2 - F | CH₃ | 91 –102 |
| 15 | 4 - Cl | CH₂Cl | 194 (× HCl) |
| 16 | 4 - Cl | CHCl₂ | 205–07 (× HCl) |
| 17 | 4-Cl | —CH₂—CH(CH₃)₂ | 232–36 (X½ naphthalene-1,5-disulfonic acid) |
| 18 | 4-Cl | —(CH₂)₁₆CH₃ | 128–41 (X½ naphthalene-1,5-disulfonic acid) |
| 19 | 4-Cl | —NH—C(CH₃)₃ | 111–15 |
| 20 | 4-Cl | —NHCH₃ | 183–190 |
| 21 | 4-Cl | —NH—(C₆H₅) | 170–173 |
| 22 | 4-Cl | —NH—(C₆H₄)—Cl | 177–185 |
| 23 | 2-Cl, 4-(C₆H₄)-Cl | CH₃ | 219–221 (× HCl) |
| 24 | 4- O | —NHCH₃ | 187 |
| 25 | 4- O | —NHC₃H₇ | 124–138 |
| 26 | 4- O | —NHC₂H₅ | 98–120 |
| 27 | 4- O | —NHC₄H₉ | 118–127 |

What is claimed is:

1. A pharmaceutical composition useful for treating mycoses in humans and animals which comprises an antimycotically effective amount of a compound of the formula

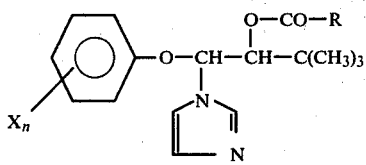

or a pharmaceutically acceptable, nontoxic salt or metal complex thereof, wherein
  R is lower alkylamino; di-lower alkylamino; or phenylamino unsubstituted or nuclear-substituted by halogen, nitro or cyano;
  X is halogen; lower alkyl; cycloalkyl of 5 to 7 carbon atoms; alkoxy of 1 to 4 carbon atoms; halogenoalkyl of 1 to 4 carbon atoms in the alkyl moiety and 1 to 5 halogen atoms; alkylthio of 1 to 4 carbon atoms; alkoxycarbonyl of 1 to 4 carbon atoms in the alkoxy moiety; phenyl unsubstituted or substituted by halo, amino, cyano, nitro or alkyl of 1 to 4 carbon atoms; phenoxy unsubstituted or nuclear-substituted by halo, amino, cyano, nitro or alkyl of 1 to 4 carbon atoms; amino, cyano, or nitro; and
  n is 0 or an integer from 1 to 5;
in combination with a pharmaceutically acceptable, non-toxic carrier suitable for administration to humans and animals.

2. A pharmaceutical composition according to claim 1 wherein
  R is alkylamino of 1 to 4 carbon atoms in the alkyl moiety, dialkylamino of 1 to 4 carbon atoms in each alkyl moiety; or phenylamino unsubstituted or nuclear-substituted by halogen, nitro or cyano;
  X is halogen; amino; cyano; nitro; alkyl of 1 to 4 carbon atoms; cycloalkyl of 5 to 7 carbon atoms; halogenoalkyl of 1 or 2 carbon atoms in the alkyl moiety and 1 to 5 halogen atoms selected from the group consisting of fluorine and chlorine; alkoxycarbonyl of 1 to 4 carbon atoms in the alkoxy moiety; alkoxy of 1 or 2 carbon atoms; alkylthio of 1 or 2 carbon atoms; phenyl unsubstituted or substituted by halogen, amino, cyano, nitro or alkyl of 1 or 2 carbon atoms; phenoxy unsubstituted or substituted by halogen, amino, cyano, nitro or alkyl of 1 or 2 carbon aroms; or phenylalkyl of 1 or 2 carbon atoms in the alkyl moiety unsubstituted or substituted in the alkyl portion by alkylcarbonyl of up to 3 carbon atoms in total and unsubstituted or substituted in the phenyl portion by halogen, nitro or cyano; and
  n is 0 or an integer from 1 to 3.

3. A pharmaceutical composition according to claim 1 wherein
  R is alkylamino of 1 or 2 carbon atoms in the alkyl moiety; dialkylamino of 1 to 4 carbon atoms in each alkyl moiety; or phenylamino unsubstituted or nuclear-substituted by halogen, nitro or cyano;
  X is halogen; amino; cyano; nitro; alkyl of 1 to 4 carbon atoms; cyclohexyl; halogenoalkyl of 1 or 2 carbon atoms in the alkyl moiety and 1 to 5 halogen atoms selected from the group consisting of fluorine and chlorine; alkoxycarbonyl of 1 to 4 carbon atoms in the alkoxy moiety; alkoxy of 1 or 2 carbon atoms; alkylthio of 1 or 2 carbon atoms; phenyl unsubstituted or substituted by halogen, amino, cyano, nitro or alkyl of 1 or 2 carbon atoms; phenoxy unsubstituted or nuclear-substituted by halogen, amino, cyano, nitro or alkyl of 1 or 2 carbon atoms; or phenylalkyl of 1 or 2 carbon atoms in the alkyl moiety unsubstituted or substituted in the alkyl portion by alkylcarbonyl of up to 3 carbon atoms in total and unsubstituted in the phenyl portion or substituted in the phenyl portion by halogen, nitro or cyano; and
  n is 0 or an integer from 1 to 3.

4. A pharmaceutical composition according to claim 1 wherein
  R is alkylamino of 1 or 2 carbon atoms; dialkylamino of 1 or 2 carbon atoms; or phenylamino unsubstituted or nuclear-substituted by chlorine;
  X is halogen; alkyl of 1 to 4 carbon atoms; cycloalkyl of 5 or 6 carbon atoms; trifluoromethyl; alkylthio of 1 or 2 carbon atoms; alkoxycarbonyl of 1 or 2 carbon atoms in the alkoxy moiety; phenyl unsubstituted or substituted by halogen; phenoxy unsubstituted or substituted by halogen; phenylalkyl of 1 or 2 carbon atoms in the alkyl moiety; or nitro; and
  n is an integer from 1 to 3.

5. A pharmaceutical composition according to claim 1 wherein
  R is alkylamino of 1 or 2 carbon atoms, dimethylamino or chlorophenylamino;
  X is chlorine, alkyl of 1 to 4 carbon atoms, cyclopentyl, cyclohexyl, trifluoromethyl, methylthio, alkoxycarbonyl of 1 or 2 carbon atoms in the alkoxy moiety, phenyl unsubstituted or substituted by halogen, phenoxy unsubstituted or substituted by halogen, benzyl or nitro; and
  n is 0 or an integer from 1 to 3.

6. A pharmaceutical composition according to claim 1 wherein the compound is in the form of a pharmaceutically acceptable salt selected from the group consisting of the hydrochloride, hydrobromide, phosphate, nitrate, acetate, maleate, succinate, fumarate, tartrate, citrate, salicylate, sorbate, lactate and 1,5-naphthalene disulfonate.

7. A pharmaceutical composition according to claim 1 wherein the compound is in the form of a metal complex wherein the metal is copper, zinc, manganese, magnesium, tin, iron or nickel.

8. A pharmaceutical composition according to claim 1 wherein
  R is alkylamino of 1 to 4 carbon atoms in the alkyl portion or phenylamino unsubstituted or nuclear-substituted by chlorine;
  X is halogen, cycloalkyl of 5 or 6 carbon atoms, phenyl or chlorophenyl; and
  n is 0 or an integer from 1 to 3.

9. A pharmaceutical composition according to claim 1 wherein
  R is methylamino, tert.-butylamino, phenylamino or chlorophenylamino;
  X is fluorine, chlorine, bromine, iodine, cyclohexyl, phenyl or chlorophenyl; and
  n is 0 or an integer from 1 to 3.

10. A pharmaceutical composition according to claim 1 wherein the compound is in racemic form.

11. A pharmaceutical composition according to claim 1 wherein the compound is in erythro form.

12. A pharmaceutical composition according to claim 1 wherein the compound is in threo form.

13. A pharmaceutical composition according to claim 1 wherein R is tert.-butylamino, X is 4-chlorine and n is 1.

14. A pharmaceutical composition according to claim 1 wherein R is methylamino, X is 4-chlorine and n is 1.

15. A pharmaceutical composition according to claim 1 wherein R is phenylamino, X is 4-chlorine and n is 1.

16. A pharmaceutical composition according to claim 1 wherein R is parachlorophenylamino, X is 4-chlorine and n is 1.

17. A method for treating mycoses in humans and animals which comprises administering to a human or animal in need thereof an antimycotically effective amount of a compound of the formula

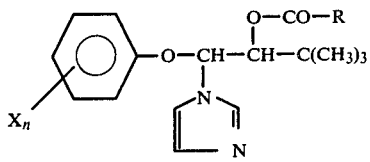

or a pharmaceutically acceptable, nontoxic salt or metal complex thereof, wherein R is lower alkylamino; di-lower alkylamino; or phenylamino unsubstituted or nuclear-substituted by halogen, nitro or cyano;

X is halogen; lower alkyl; cycloalkyl of 5 to 7 carbon atoms; alkoxy of 1 to 4 carbon atoms; halogenoalkyl of 1 to 4 carbon atoms in the alkyl moiety and 1 to 5 halogen atoms; alkylthio of 1 to 4 carbon atoms; alkoxycarbonyl of 1 to 4 carbon atoms in the alkoxy moiety; phenyl unsubstituted or substituted by halo, amino, cyano, nitro or alkyl of 1 to 4 carbon atoms; phenoxy unsubstituted or nuclear-substituted by halo, amino, cyano, nitro or alkyl of 1 to 4 carbon atoms; amino, cyano, or nitro; and n is 0 or an integer from 1 to 5; in combination with a pharmaceutically acceptable, non-toxic carrier suitable for administration to humans and animals.

18. A method according to claim 17 wherein
R is alkylamino of 1 to 4 carbon atoms in the alkyl moiety, dialkylamino of 1 to 4 carbon atoms in each alkyl moiety; or phenylamino unsubstituted or nuclear-substituted by halogen, nitro or cyano;

X is halogen; amino; cyano; nitro; alkyl of 1 to 4 carbon atoms; cycloalkyl of 5 to 7 carbon atoms; halogenoalkyl of 1 or 2 carbon atoms in the alkyl moiety and 1 to 5 halogen atoms selected from the group consisting of fluorine and chlorine; alkoxycarbonyl of 1 to 4 carbon atoms in the alkoxy moiety; alkoxy of 1 or 2 carbon atoms; alkylthio of 1 or 2 carbon atoms; phenyl unsubstituted or substituted by halogen, amino, cyano, nitro or alkyl of 1 or 2 carbon atoms; phenoxy unsubstituted or substituted by halogen, amino, cyano, nitro or alkyl of 1 or 2 carbon aroms; or phenylalkyl of 1 or 2 carbon atoms in the alkyl moiety unsubstituted or substituted in the alkyl portion by alkylcarbonyl of up to 3 carbon atoms in total and unsubstituted or substituted in the phenyl portion by halogen, nitro or cyano; and n is 0 or an integer from 1 to 3.

19. A method according to claim 17 wherein
R is alkylamino of 1 or 2 carbon atoms in the alkyl moiety; dialkylamino of 1 to 4 carbon atoms in each alkyl moiety; or phenylamino unsubstituted or nuclear-substituted by halogen, nitro or cyano;

X is halogen; amino; cyano; nitro; alkyl of 1 to 4 carbon atoms; cyclohexyl; halogenoalkyl of 1 or 2 carbon atoms in the alkyl moiety and 1 to 5 halogen atoms selected from the group consisting of fluorine and chlorine; alkoxycarbonyl of 1 to 4 carbon atoms in the alkoxy moiety; alkoxy of 1 or 2 carbon atoms; alkylthio of 1 or 2 carbon atoms; phenyl unsubstituted or substituted by halogen, amino, cyano, nitro or alkyl of 1 or 2 carbon atoms; phenoxy unsubstituted or nuclear-substituted by halogen, amino, cyano, nitro or alkyl of 1 or 2 carbon atoms; or phenylalkyl of 1 or 2 carbon atoms. in the alkyl moiety unsubstituted or substituted in the alkyl portion by alkylcarbonyl of up to 3 carbon atoms in total and unsubstituted in the phenyl portion or substituted in the phenyl portion by halogen, nitro or cyano; and n is 0 or an integer from 1 to 3.

20. A method according to claim 17 wherein
R is alkylamino of 1 or 2 carbon atoms; dialkylamino of 1 or 2 carbon atoms; or phenylamino unsubstituted or nuclear-substituted by chlorine;

X is halogen; alkyl of 1 to 4 carbon atoms; cycloalkyl of 5 or 6 carbon atoms; trifluoromethyl; alkylthio of 1 or 2 carbon atoms; alkoxycarbonyl of 1 or 2 carbon atoms in the alkoxy moiety; phenyl unsubstituted or substituted by halogen; phenoxy unsubstituted or substituted by halogen; phenylalkyl of 1 or 2 carbon atoms in the alkyl moiety; or nitro; and n is an integer from 1 to 3.

21. A method according to claim 17 wherein
R is alkylamino of 1 or 2 carbon atoms, dimethylamino or chlorophenylamino;

X is chlorine, alkyl of 1 to 4 carbon atoms, cyclopentyl, cyclohexyl, trifluoromethyl, methylthio, alkoxycarbonyl of 1 or 2 carbon atoms in the alkoxy moiety, phenyl unsubstituted or substituted by halogen, phenoxy unsubstituted or substituted by halogen, benzyl or nitro; and n is 0 or an integer from 1 to 3.

22. A method according to claim 17 wherein the compound is in the form of a pharmaceutically acceptable salt selected from the group consisting of the hydrochloride, hydrobromide, phosphate, nitrate, acetate, maleate, succinate, fumarate, tartrate, citrate, salicylate, sorbate, lactate and 1,5-naphthalene disulfonate.

23. A method according to claim 17 wherein the compound is in the form of a metal complex wherein the metal is copper, zinc, manganese, magnesium, tin, iron or nickel.

24. A method according to claim 17 wherein
R is alkylamino of 1 to 4 carbon atoms in the alkyl portion or phenylamino unsubstituted or nuclear-substituted by chlorine;

X is halogen, cycloalkyl of 5 or 6 carbon atoms, phenyl or chlorophenyl; and n is 0 or an integer from 1 to 3.

25. A method according to claim 17 wherein
R is methylamino. tert.-butylamino, phenylamino or chlorophenylamino;

X is fluorine, chlorine, bromine, iodine, cyclohexyl, phenyl or chlorophenyl; and n is 0 or an integer from 1 to 3.

26. A method according to claim 17 wherein the compound is in racemic form.

27. A method according to claim 17 wherein the compound is in erythro form.

28. A method according to claim 17 wherein the compound is in threo form.

29. A method according to claim 17 wherein R is tert.-butylamino, X is 4-chlorine and n is 1.

30. A method according to claim 17 wherein R is methylamino, X is 4-chlorine and n is 1.

31. A method according to claim 17 wherein R is phenylamino, X is 4-chlorine and n is 1.

32. A method according to claim 17 wherein R is parachlorophenylamino, X is 4-chlorine and n is 1.

33. A pharmaceutical composition according to claim 1 in parenteral administration form.

34. A pharmaceutical composition according to claim 1 in intravenous administration form.

35. A method according to claim 17 wherein the administration is parenteral.

36. A method according to claim 17 wherein the administration is intravenous.

* * * * *